(12) United States Patent
Lu et al.

(10) Patent No.: US 8,460,564 B2
(45) Date of Patent: Jun. 11, 2013

(54) DRUG DELIVERY CHIP AND FABRICATING METHOD THEREOF

(75) Inventors: Shey-Shi Lu, Taipei (TW); Yao-Joe Yang, Taipei (TW); Yu-Jie Huang, Taipei (TW); Chii-Wann Lin, Taipei (TW); Hsin-Hung Liao, Taipei (TW); Tao Wang, Taipei (TW); Pen-Li Huang, Taipei (TW); Yao-Hong Wang, Taipei (TW)

(73) Assignee: National Taiwan University, Taipei (TW)

( * ) Notice: Subject to any disclaimer, the term of this patent is extended or adjusted under 35 U.S.C. 154(b) by 486 days.

(21) Appl. No.: 12/695,516

(22) Filed: Jan. 28, 2010

(65) Prior Publication Data

US 2010/0312229 A1    Dec. 9, 2010

(30) Foreign Application Priority Data

Jun. 6, 2009   (TW) ................................ 98118885 A

(51) Int. Cl.
*B44C 1/22*      (2006.01)
*A61M 5/14*     (2006.01)

(52) U.S. Cl.
USPC ........ 216/17; 216/2; 216/13; 216/41; 216/58; 216/83; 604/891.1

(58) Field of Classification Search
USPC .............. 216/2, 13, 41, 58, 83, 17; 604/891.1
See application file for complete search history.

(56) References Cited

U.S. PATENT DOCUMENTS

| 6,123,861 A * | 9/2000 | Santini et al. ................. 216/2 |
| 6,773,429 B2 * | 8/2004 | Sheppard et al. .......... 604/891.1 |
| 2003/0143444 A1 * | 7/2003 | Liu et al. ......................... 429/19 |
| 2008/0115559 A1 * | 5/2008 | Santini et al. .................. 73/1.03 |

OTHER PUBLICATIONS

Yang et al., "A Release-on-Demand Wireless CMOS Drug Delivery SoC Based on Electrothermal Activation Technique", 2009 IEEE International Solid-State Circuits Conference.

* cited by examiner

*Primary Examiner* — Shamim Ahmed
(74) *Attorney, Agent, or Firm* — Edwards Wildman Palmer LLP; Peter F. Corless; Steven M. Jensen

(57) ABSTRACT

A drug-delivery chip and a method of fabricating the same are provided. The drug-delivery chip has a main body having at least one drug receiving space individually formed with an opening for storing drugs therein; a thin film for sealing up the at least one drug receiving space; a first conductive wire connecting to one end of the thin film; a second conductive wire connecting to another end of the thin film; a signal-receiving module for receiving actuated signals; and a control module for applying voltages to first and second wire conductive s according to the actuated signal, thereby generating heat to break off the thin film for the release of a drug or drugs received in the at least one drug receiving space.

7 Claims, 8 Drawing Sheets

DRUG DELIVERY CHIP AND FABRICATING METHOD THEREOF

CROSS-REFERENCES TO RELATED APPLICATIONS

This application claims under 35 U.S.C. §119(a) the benefit of Taiwanese Application No. 98118885 filed Jun. 6, 2009 the entire contents of which is incorporated herein by reference.

BACKGROUND OF THE INVENTION

1. Field of the Invention

This invention relates to drug-delivery chips and methods of fabricating the same, and more particularly, to a drug-delivery chip and a method of fabricating the drug-delivery chip which employ a semiconductor rear fabrication process technique.

2. Description of Related Art

The advance of technologies brings a great convenience to ordinary people, but it also contaminates the environment and increases the possibility that people get ill. In the early age, people suffer from short lifespan because the medical instruments are not mature or popular and people cannot be well treated when getting ill. As the medical technology makes a lot of progress in recent years, people live healthier and longer than they did before, and the population of the senior citizens increases dramatically, which booms the need of a variety of medicines.

People may buy non-prescription medicines, such as a drinking medicine, dropping medicine and external medicine, at a drugstore and take these drugs by themselves. A chronic disease patient such as a hypertension patient has to take oral anti-hypertension drugs regularly. A diabetes patient has to take oral hypoglycemic drugs or even gets a shot of insulin. A cardiopathy patient has to take medicines regularly, especially in a moment when a heart attack happens.

Taking oral drugs or getting a shot of drugs regularly is vitally important for the chronic disease patients, critically ill patients and those who needs to take certain drugs, especially for the senior citizens who suffer from many kinds of illness and have to take as many as eight pills of drugs every day. Sometimes they forgot taking medicines, or forgot that they have already took the medicines and took the medicines a second time.

Cancer is one of the leading death causes for human. In addition to the electrotherapy, chemotherapy and surgical operation, the treatment to cancer also includes taking cancer drugs and analgesia medicine regularly. The drugs are swallowed and absorbed by human body through the digestive system, or are injected into the veins and reach the affected region via the blood circulation. The drugs are thus diluted. In order to reach the treatment dosage requirement, the patient has to take a variety of drugs and suffers from painful side effects.

A drug-delivery controlling circuit is developed for the treatment of cancer. The drug-delivery controlling circuit controls the delivery of drugs by connecting a circuit board to a controller and/or a signal receiver. The drug-delivery controlling circuit can be implanted into human body via a surgical operation, for the treatment of cancer.

However, the prior art has the following problems:

(1) high cost—since the controller and the signal receiver have to be fabricated individually and a drug storage part controlled by the controller is integrated into the circuit board;

(2) bulky volume—since the controller, the signal receiver and the drug storage part are all connected to the circuit board and packaged together, such a bulky package cannot be implanted into human body easily and, even if it can be implanted into human body, if will make harmful impacts on human body; and (3) cannot provide a variety of drugs—since the controller, the signal receiver and the drug storage part controlled by the controller are all connected to the circuit board, the circuit board is limited to have a small size, such that the requirement of providing a variety of drugs cannot be met.

Therefore, how to provide a drug-delivery technique that is miniaturized, has a low cost and can be remotely control to deliver drugs at predetermined time and in determined kinds is becoming one of the most urgent issues in the art.

SUMMARY OF THE INVENTION

In view of the above-mentioned problems of the prior art, the present invention provides a miniaturized drug-delivery chip and a method of fabricating the same.

According to a embodiment of the present invention, the drug-delivery chip includes a main body having at least one drug receiving space individually formed with an opening; a thin film for sealing up the opening of the at least one drug receiving space; a first conductive wire connected to one end of the thin film; a second conductive wire connected to another end of the thin film; a signal-receiving module for receiving actuated signals; and a control module for applying voltages to the first conductive wire and then the second conductive wire according to the actuated signals, thereby generating heat to break off the thin film for the release of a drug (or drugs) received in the at least one receiving space from the opening.

According to another embodiment of the present invention, the present invention provides a drug-delivery chip that includes a main body having at least one drug receiving space individually formed with an opening; a first conductive wire connected to a side wall of the at least one drug receiving space; a second conductive wire connected to another side wall of the at least one drug receiving space and spaced from the first conductive wire; a thin film for sealing up the opening of the at least one drug receiving space; a signal-receiving module for receiving actuated signals; and a control module for applying voltages to the first conductive wire and the second conductive wire according to the actuated signals, thereby electrolyzing a drug (or drugs) received in the at least one drug receiving space and generating air to break off the thin film for the release of the drugs from the opening of the at least one receiving space.

The method of fabricating the drug-delivery chip includes the steps of: providing a substrate having a stack structure formed on a first surface of the substrate, the stack structure having an insulation layer, a conductive wire layer having void spaces, and a protection layer; etching the protection layer at a position corresponding to the void spaces of the conductive wire layer to form an opening; forming a metal thin film on the conductive wire layer to seal up the opening, wherein the metal thin film has two ends respectively connected to the conductive wire layer on each of two sides of the opening and is electrically connected to a control module via the conductive wire layer; etching the substrate and the insulation layer to form a drug receiving space and expose the metal thin film; filling the drug receiving space with a drug (or drugs); and installing a sealing film on a second surface of the substrate to seal up the drug filled in the drug receiving space.

The present invention further provides a method of fabricating the drug-delivery, including the steps of: providing a substrate having a stack structure on a first surface of the substrate, the stack structure having an insulation layer, a conductive wire layer having void spaces, and a protection layer; etching the substrate and the insulation layer at a position corresponding to the void spaces of the conductive wire layer to form a drug receiving space; filling the drug receiving space with a drug (drugs); and installing a sealing film on a second surface of the substrate to seal up the drugs filled in the drug receiving space.

Compared with the prior art, the present invention provides a drug-delivery chip and a method of fabricating the same, which employ a semiconductor rear fabrication process technique to form a drug receiving space on a drug-delivery chip having a control module and a signal-receiving module, so as to achieve the effectiveness of miniaturization, low cost, and the controlling of the drug-delivery time and the kind of drugs to be delivered.

DETAILED DESCRIPTION OF PREFERRED EMBODIMENTS

The following illustrative embodiments are provided to illustrate the disclosure of the present invention, these and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

Figure 1A:
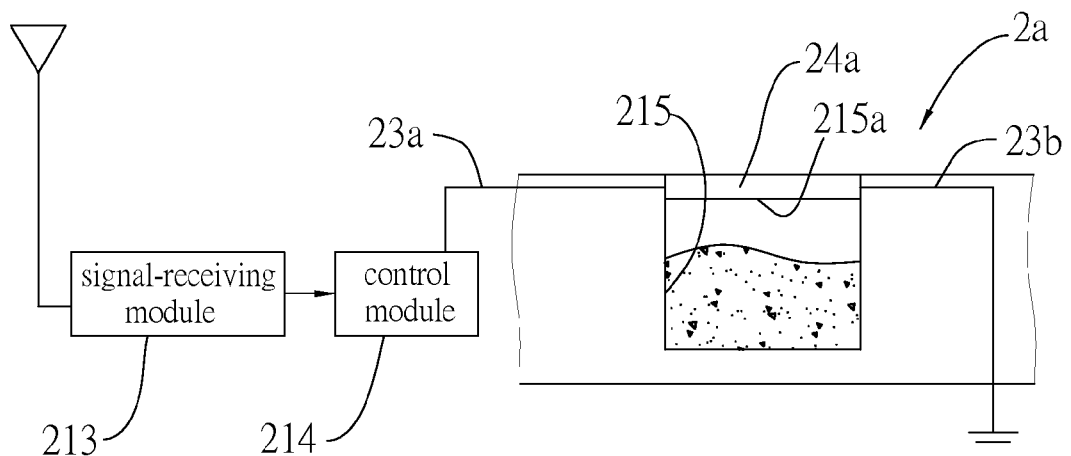
FIG. 1A is a schematic diagram of a drug-delivery chip of an embodiment according to the present invention.

Please refer to FIG. 1A, which is a schematic diagram of a drug-delivery chip of an embodiment according to the present invention. Preferably, the drug-delivery chip of the present invention is a system-on-a-chip (SoC) fabricated by a 0.35 μm CMOS process, and has a size of 1.77 mm×1.4 mm.

In the embodiment of the present invention, the drug-delivery chip comprises a main body 2a having at lease a drug receiving space 215 for storing drugs therein, a thin film 24a for sealing up an opening 215a of the drug receiving space 215, a first conductive wire 23a connected to one end of the thin film 24a, a second conductive wire 23b connected to another end of the thin film 24a, a signal-receiving module 213 for receiving actuated signals, and a control module 214 for controlling the release of the drugs received in the drug receiving space 215 according to the actuated signals.

In an embodiment of the present invention, the thin film 24a is a metal thin film. In practice, when the signal-receiving module 213 receives the actuated signals, the control module 214 applies voltages to the first conductive wire 23a and the second conductive wire 23b, allowing currents to pass through the first conductive wire 23a and the second conductive wire 23b. In consequence, the drugs can be released from the opening 215a of the drug receiving space 215, since the heat generated by the first conductive wire 23a and the second conductive wire 23b accumulates on the metal thin film 24a and eventually breaks off the metal thin film 24a.

Figure 1B:
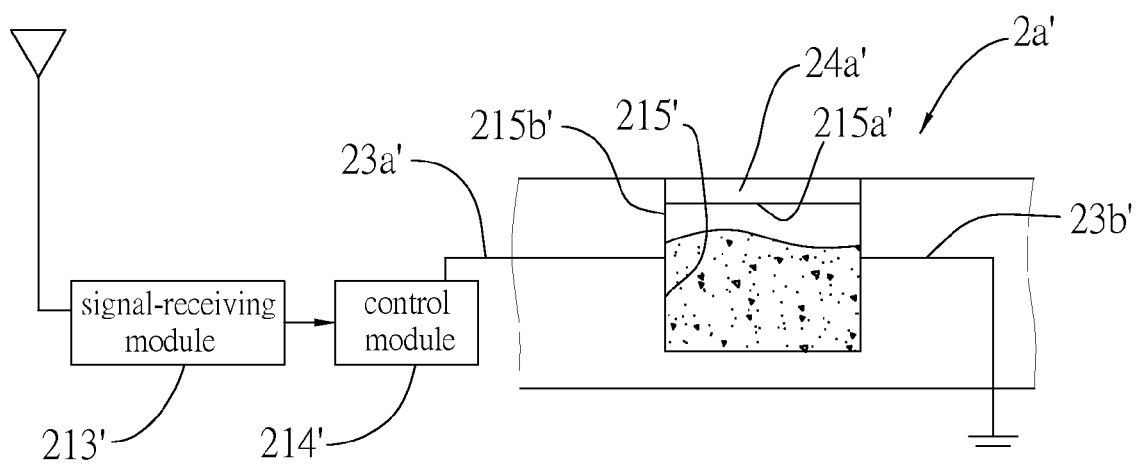
FIG. 1B is a schematic diagram of a drug-delivery chip of another embodiment according to the present invention.

Please refer to FIG. 1B, which is a schematic diagram of a drug-delivery chip of another embodiment according to the present invention. In the another embodiment of the present invention, the drug-delivery chip comprises a first conductive wire 23a', a second conductive wire 23b', a drug receiving space 215', a thin film 24a' for sealing up an opening 215a' of the drug receiving space 215', a signal-receiving module 213' for receiving actuated signals, and a control module 214' for controlling the release of the drugs received in the drug receiving space 215' according to the actuated signals.

In the another embodiment of the present invention, the first conductive wire 23a' and the second conductive wire 23b' are connected to side walls 215b' on two sides of the drug receiving space 215', respectively. In yet another embodiment of the present invention, the first conductive wire 23a' and the second conductive wire 23b' are both connected to an identical side wall of the drug receiving space 215', such as a bottom surface or the same side wall. In the another embodiment, the thin film 24a' is a protection layer of the drug-delivery chip, and the drugs received in the drug receiving space 215' contain moisture.

In practice, when the signal-receiving module 213' receives the actuated signals, the control module 214' applies voltages to the first conductive wire 23a' and the second conductive wire 23b', enabling the moisture contained in the drugs received in the drug receiving space 215' to be electrolyzed and generate bubbles, leading the thin film 24a' of the drug-delivery chip to be broken off, such that the drugs can be released from the opening 215a' of the drug receiving space 215'.

Note that the drug-delivery chip of the present invention is not limited to have only one drug receiving space 215 (or 215'), as shown in FIGS. 1A and 1B. A drug-delivery chip according to the present invention may have any number of drug receiving spaces 215 (or 215'). Further, the drug receiving space 215 (or 215') may receive a variety of drugs.

Figure 2:
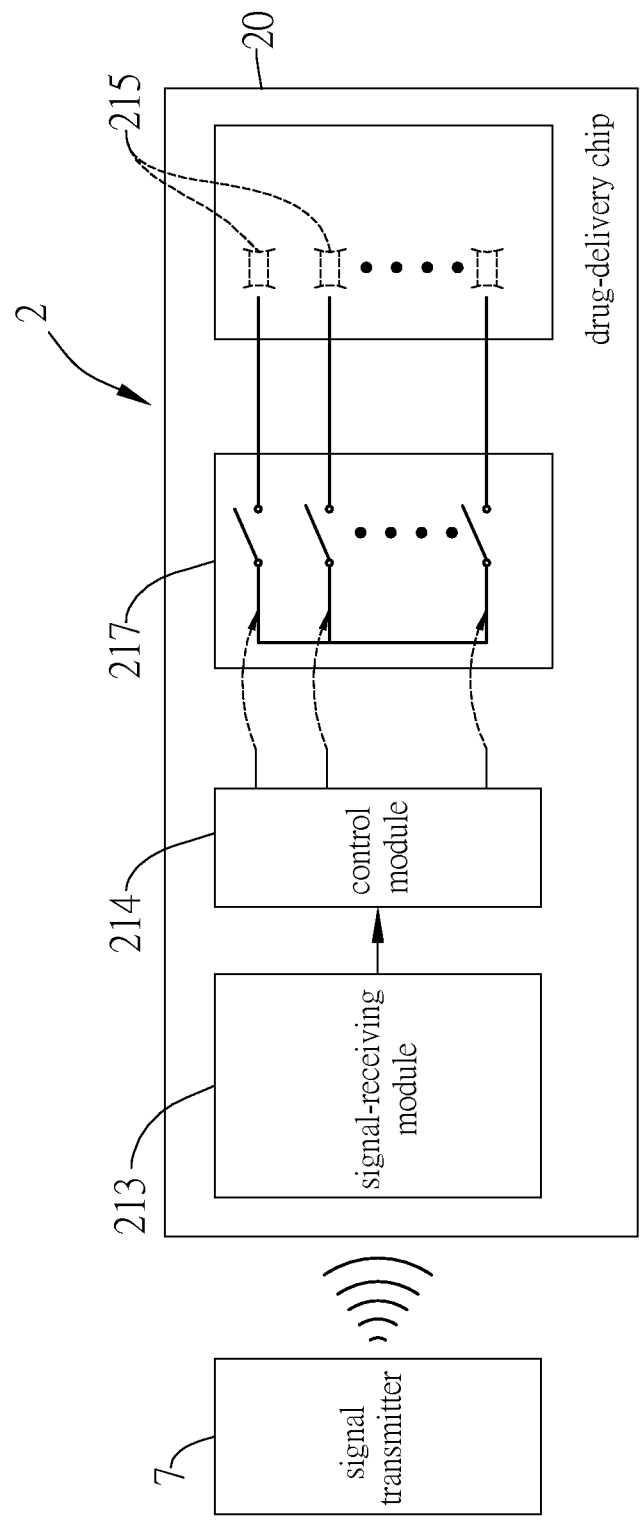
FIG. 2 is a functional block diagram of a drug-delivery chip cooperating with a signal transmitter of an embodiment according to the present invention.

FIG. 2 is a functional block diagram of a drug-delivery chip cooperating with a signal transmitter 7 of an embodiment according to the present invention. Note that the embodiment shown in FIG. 2 is exemplified based on the drug-delivery chip shown in FIG. 1A. As shown in FIG. 2, the drug-delivery chip of the embodiment comprises a plurality of drug receiving spaces 215, and a plurality of switching units 217 connected to the control module 214. The switching units 217 are further connected to one end of a plurality of metal thin films 24a for sealing up the drug receiving spaces 215 and a first conductive wire 23a in a one-to-one manner. The another end of the metal thin films 24a is connected to the second conductive wire 23b that acts as a ground end. The signal transmitter 7 is, for example, a remote controller, for transmitting the actuated signals to the signal-receiving module 213 of the drug-delivery chip. The signal transmitter 7 may be integrated into an electronic apparatus (not shown), such as a mobile phone, a personal digital assistant or a computer, that can transmit the actuated signals.

Since the drug-delivery chip of the embodiment comprises a plurality of drug receiving spaces 215, in order for the control module 214 to identify the actuated signals received and control the release of the drugs received in any one or more than one of the drug receiving spaces 215, the actuated signals transmitted by the signal transmitter 7 may comprise check codes or/and address codes. Therefore, the control module 214 identifies the check codes of the actuated signals after the signal-receiving module 213 receives the actuated signals, so as to prevent the drug-delivery chip, under a circumstance that the wireless communication is interfered due to external interference signals, from performing erroneous actions, such as releasing the wrong drugs or releasing the drugs without any reason. After identifying the check codes to be correct (which means that the check codes are valid), the control module 214 turns on the corresponding switching unit 217 according to the address codes of the actuated signals, such that currents can flow through the turned-on switching unit 217 to the first conductive wire 23a connected to the turned-on switching unit 217. Therefore, the first conductive wire 23a connected to the turned-on switching unit 217 is electrified, the metal thin film 24a connected to the electrified first conductive wire 23a is broken off, and the drug receiving space 215 corresponding to the broken-off metal thin film 24a can release the drugs.

Further, the actuated signals further comprise drug-delivery time messages. The control module 214 receives and stores the drug-delivery time messages of the actuated signals, and controls the release of the drugs received in the drug receiving space 215 at predetermined time. Therefore, the drug-delivery time may be set by transmitting the actuated signals externally at predetermined time, by appending the drug-delivery time messages to the actuated signals and transmitting the actuated signals regularly, or embedding a predetermined drug-delivery time program into the control module 214 to control the release the drugs received in the drug receiving space 215.

Note that in the embodiment shown in FIG. 1A, the thin film 24a is broken off in a current heating and melting way. In this way, when the control module 214 turns on the corresponding switching unit 217 according to the address codes of the actuated signals, currents will flow through the conductive wire 23a and 23b electrically connected to the turned-on switching unit 217, since both ends of the metal thin film 24a are connected to the first conductive wire 23a and the second conductive wire 23b, respectively. Then, heat generated by the currents accumulates on the metal thin film 24a and the metal thin film 24a is broken off, such that the drugs received in the drug receiving space 215 under the metal thin film 24a may be released. In the embodiment shown in FIG. 1B, the thin film 24a is broken off in an electrolyzed way. In this way, the protection layer of the drug-delivery chip is employed as the thin film to seal up the drug receiving space 215'. Since the first conductive wire 23a' and the second conductive wire 23b' are connected to the side wall 215b' of the drug receiving space 215', when the control module 214' turns on the corresponding switching unit 217' according to the address codes of the actuated signals, currents will flow through the conductive wire 23a' and 23b' electrically connected to the turned-on switching unit 217', leading the moisture contained in the drugs received in the drug receiving space 215' to be electrolyzed and generate enough bubbles to break off the protection layer 24a'. Therefore, the drugs may be released from the drug receiving space 215' under the protection layer.

It can be known from the above embodiments that the drug-delivery chip according to the present invention integrates the control module and the signal-receiving module with the drug receiving space, so as to achieve the objectives of miniaturization, low cost and the controlling of drug-delivery time and the kind of the drugs to be delivered.

Please refer to FIGS. 3A-3I, which are schematic diagrams illustrating a method of fabricating a drug-delivery chip of an embodiment according to the present invention. The method of fabricating the drug-delivery chip is applicable to the fabrication of a drug-delivery chip that releases drugs received in a drug receiving space in a current heating and melting way.

Figure 3A:
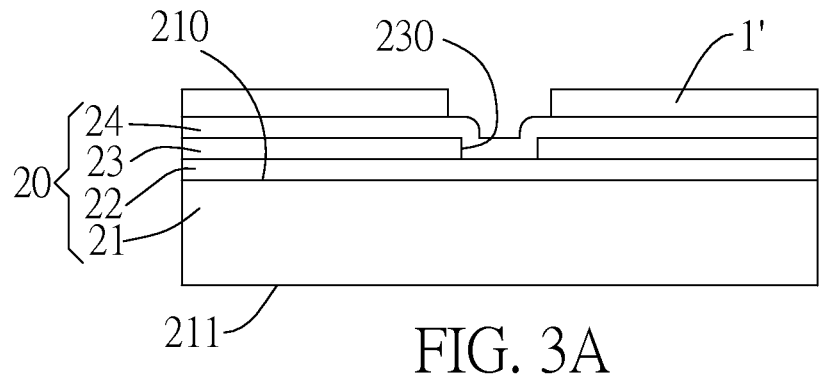
FIGS. 3A-3I are schematic diagrams of a method of fabricating a drug-delivery chip of an embodiment according to the present invention.

The step shown in FIG. 3A is executed first: providing a main body 20, the main body 20 comprising a substrate 21 having a first surface 210 and a second surface 211 opposed to the first surface 210, an insulation layer 22 (e.g., an oxide layer or nitride) installed on the first surface 210 of the substrate 21, a conductive wire layer 23 installed on the insulation layer 22 and having void spaces 230, and a protection layer 24 that covers the conductive wire layer 23.

A first masking layer 1' is installed on the protection layer 24 of the main body 20. The first masking layer 1' has breach patterns corresponding to the position of the void spaces 230 of the conductive wire layer 23, for exposing the protection layer 24.

Figure 3B:
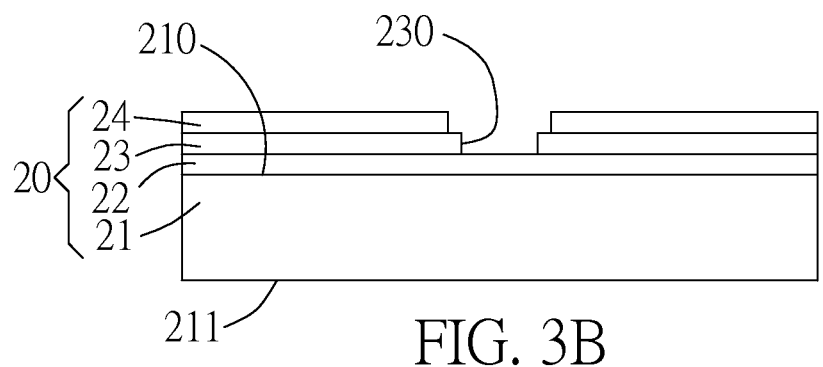

The step shown in FIG. 3B is executed next: etching the protection layer 24 with a reactive ion etching (RIE) technique, to expose the void spaces 230 of the conductive wire layer 23 and the insulation layer 22 under the void spaces 230, and removing the first masking layer 1'.

Figure 3C:
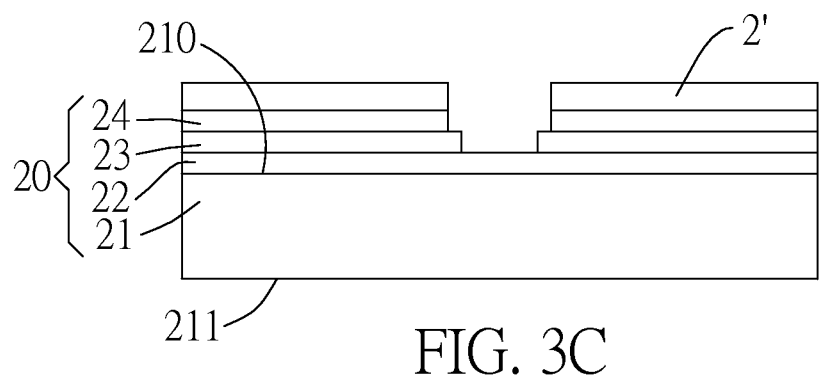

The step shown in FIG. 3C is executed next: covering the protection layer 24 with a second masking layer 2'.

Figure 3D:
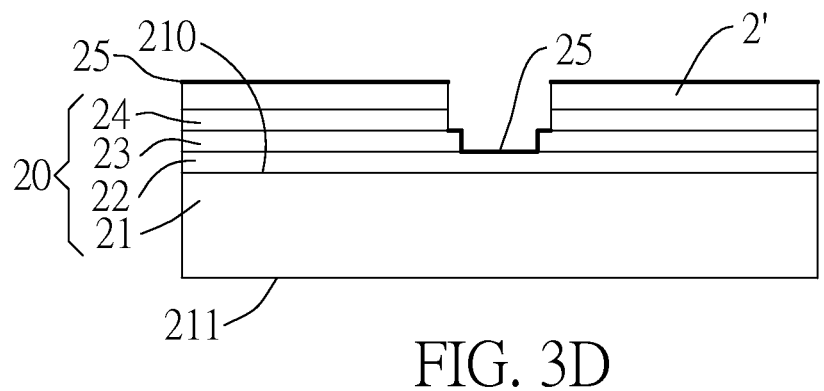

The step shown in FIG. 3D is executed next: forming a metal thin film 25, with an evaporation technique, on the second masking layer 2' and on the conductive wire layer 23 and the void spaces 230 of the conductive wire layer 23 that expose to a region outside of the protection layer 24, and connecting both ends of the metal thin film 25 to the conductive wire layer 23 on two ends of the void spaces 230, respectively.

Figure 3E:
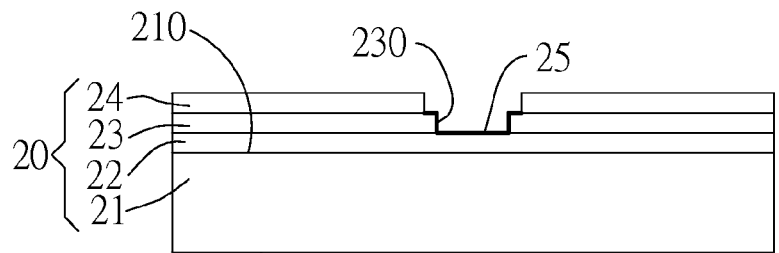

The step shown in FIG. 3E is executed next: removing the second masking layer 2' with a lift-off technique.

Figure 3F:
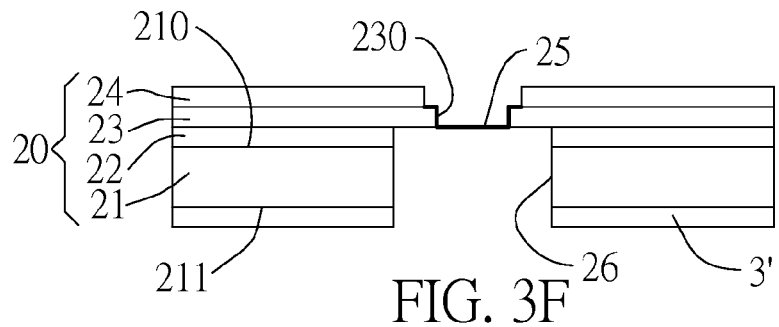

The step shown in FIG. 3F is executed next: installing a third masking layer 3' on the second surface 211 of the substrate 21, the third masking layer 3' having breach patterns corresponding to the position of the void spaces 230 of the conductive wire layer 23, etching the substrate 21 and the insulation layer 22 with an etching technique to expose a part of the metal thin film 25 that is formed in the void spaces 230 of the conductive wire layer 23 and toward the substrate 21, and forming among the substrate 21, the insulation layer 22 and metal thin film 25 a drug receiving space 26 for storing drugs therein.

The substrate 21 is etched by an inductively-coupled plasma (ICP) technique, while the insulation layer 22 is etched by a reactive ion etching (RIE) technique. Before the above etching techniques are performed, a chemical-mechanical polishing (CMP) technique may be employed to polish the second surface 211 of the substrate 21, so as to thin the substrate 21 and speed up the etching.

Figure 3G:
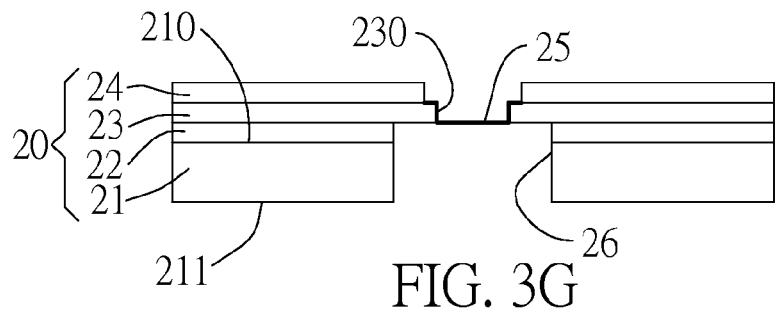

The step shown in FIG. 3G is executed next: removing the third masking layer 3'.

Figure 3H:
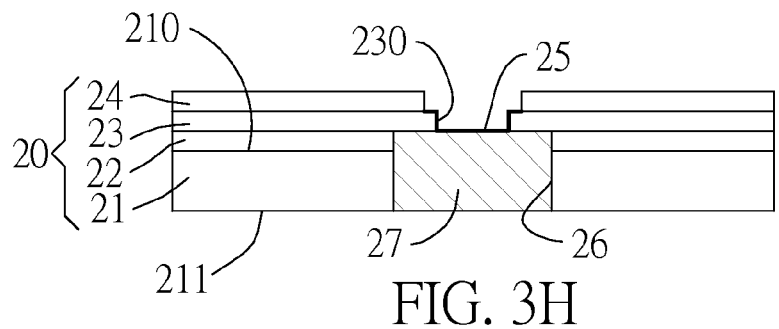

The step shown in FIG. 3H is executed next: filling the drug receiving space 26 with drugs 27.

Figure 3I:
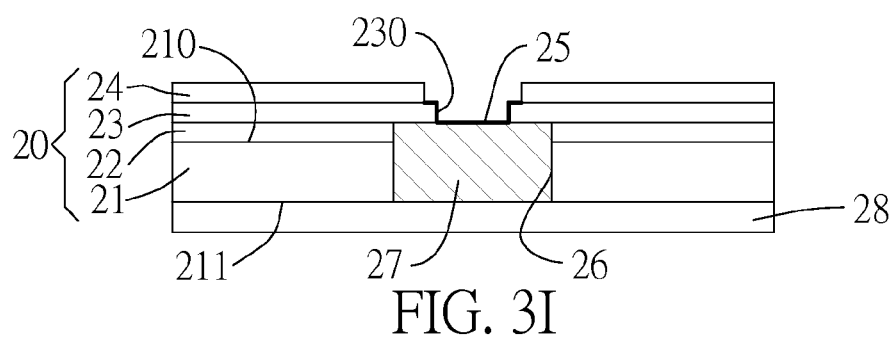

The step shown in FIG. 3I is executed next: installing a thin film 28 on the second surface 211 of the substrate 21 to seal up the drugs 27 filled in the drug receiving space 26.

Figure 4:
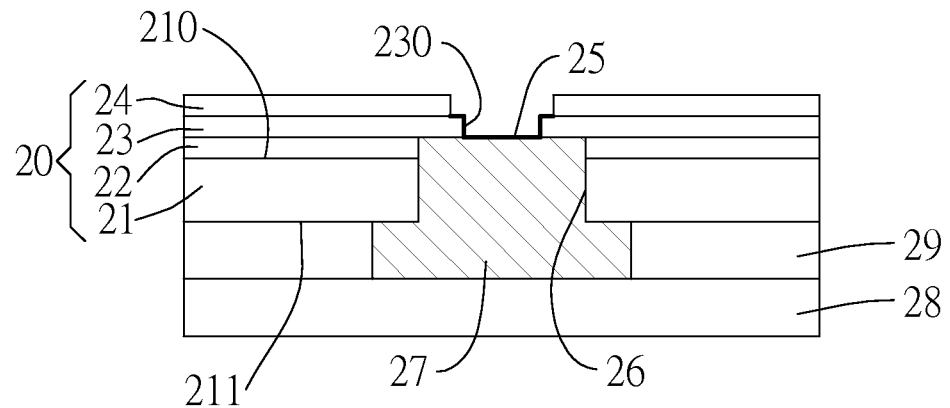
FIG. 4 is a schematic diagram illustrating a step of enlarging a drug receiving space of the drug-delivery chip shown in FIG. 3I.

Please refer to FIG. 4, which is a schematic diagram illustrating a step of enlarging the drug receiving space 26 of the drug-delivery chip. As shown in FIG. 4, a plate layer 29 is installed on the second surface 211 of the substrate 21 at a side edge opposed to a position where the drug receiving space 26 is formed, to enlarge the storage capacity of the drug receiving space 26. The thin film 28 is further installed to seal up the drugs 27 filled in the drug receiving space 26.

In the method of fabricating a drug-delivery chip shown in FIG. 3A, the breach patterns of the first masking layer 1' are not limited to correspond to the position of the void spaces 230 of the conductive wire layer 23. The breach patterns of the first masking layer 1' may be installed to correspond to a position of the two conductive wire layers 23, which is in an open state after the first masking layer 1' is etched and is in a close state after the metal thin film 25 is formed and is supplied with electricity.

Figure 5A:
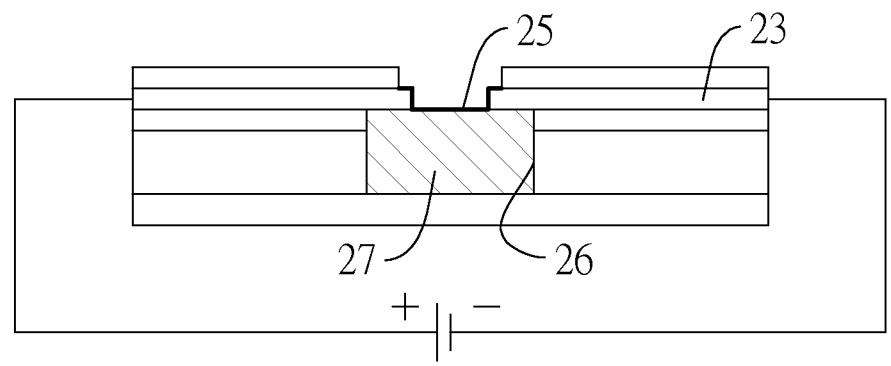
FIGS. 5A and 5B are schematic diagrams illustrating the way that the drug-delivery chip fabricated by the method shown in FIGS. 3A-3I releases drugs.
Figure 5B:
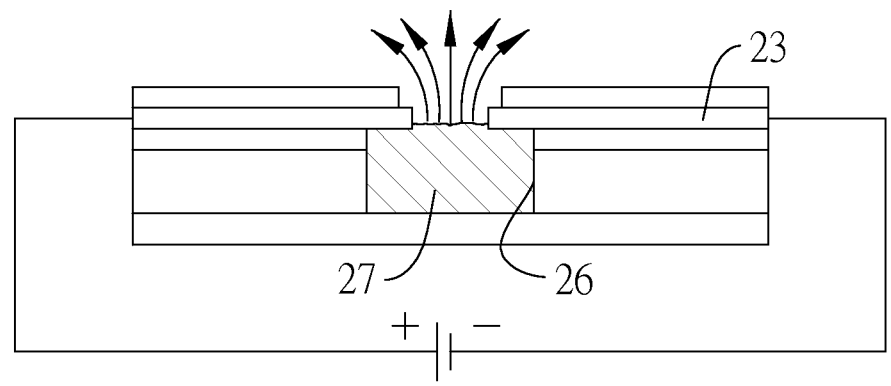

FIGS. 5A and 5B illustrate the way that the drug-delivery chip fabricated by the method of fabricating a drug-delivery chip releases drugs.

As shown in FIG. 5A, the control module applies voltages to the conductive wire layer 23 according to the actuated signals.

As shown in FIG. 5B, break off the metal thin film 25 that is connected to the conductive wire layer 23 and covers the drug receiving space 26 to release the drugs 27 received in the drug receiving space 26.

It can be known from FIGS. 3A-3I, FIG. 4 and FIGS. 5A-5B that the position of the void spaces 230 of the conductive wire layer 23 is selected as the releasing exits for the drugs received in the drug receiving space 26. If the drug-delivery chip has a plurality of drug receiving spaces 26, the drug-delivery chip may further comprise a plurality of switching units connected in a one-to-one manner to the plurality of the drug receiving spaces 26. When the signal-receiving module receives the actuated signals that have check codes, address codes and/or predetermined time messages, the control module turns on the corresponding switching unit at predetermined time according to the actuated signals, such that currents will flow through the metal thin film 25 that is connected to the conductive wire layer 23 and covers the drug receiving space 26, leading the metal thin film 25 to be broken off for the drugs 27 to be released.

The metal thin film 25 is broken off because of the passing of great enough currents through the metal thin film 25. Since the metal thin film 25 is far thinner than the conductive wire layer 23 and the metal thin film 25 has a resistance far greater than a resistance of the conductive wire layer 23, when the great enough currents are passing, a great amount of heat will be generated and accumulate on the metal thin film 25, and break the metal thin film 25 eventually, such that the drugs 27 may be released. The drugs 27 are in a solid state (powder) or in a liquid state.

FIGS. 6A-6D are schematic diagrams of a method of fabricating a drug-delivery chip of another embodiment according to the present invention. The method of fabricating a drug-delivery chip is applicable to the fabrication of a drug-delivery chip that releases drugs received in a drug receiving space in an electrolyzed way.

Figure 6A:
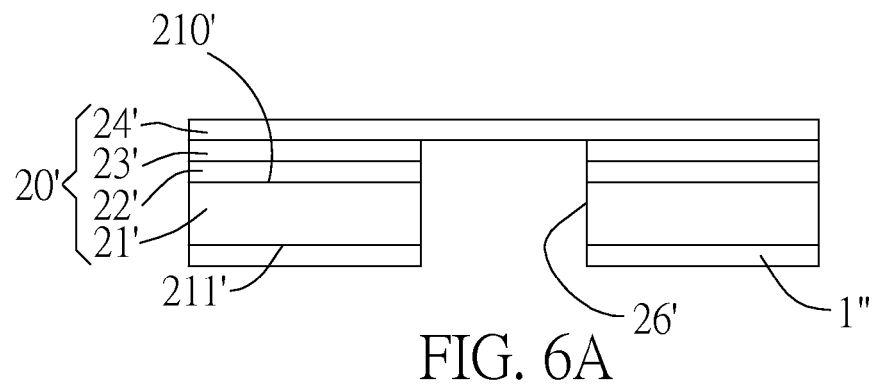
FIGS. 6A-6D are schematic diagrams of a method of fabricating a drug-delivery chip of another embodiment according to the present invention.

The step shown in FIG. 6A is executed first: providing a main body 20' that comprises a substrate 21' having a first surface 210' and a second surface 211' opposed to the first surface 210', an insulation layer 22' installed on the first surface 210' of the substrate 21', a conductive wire layer 23' installed on the insulation layer 22', and a protection layer 24' that covers the conductive wire layer 23'.

A first masking layer 1'' is installed at a predetermined position on the second surface 211' of the substrate 21' of the main body 20'. The first masking layer 1'' has breach patterns. A part of the protection layer 24' toward the first surface of the substrate 21' is exposed by etching the substrate 21' and the insulation layer 22' with an etching technique, and a drug receiving space 26' is formed among the substrate 21', the insulation layer 22', the conductive wire layer 23' and the protection layer 24' for storing drugs.

The substrate 21' is etched by an inductively-coupled plasma technique, while the insulation layer 22' is etched by a wet-etching technique. Before the above etching techniques are performed, a chemical-mechanical polishing technique may be employed to polish the second surface 211' of the substrate 21', so as to thin the substrate 21' and speed up the etching.

Figure 6B:
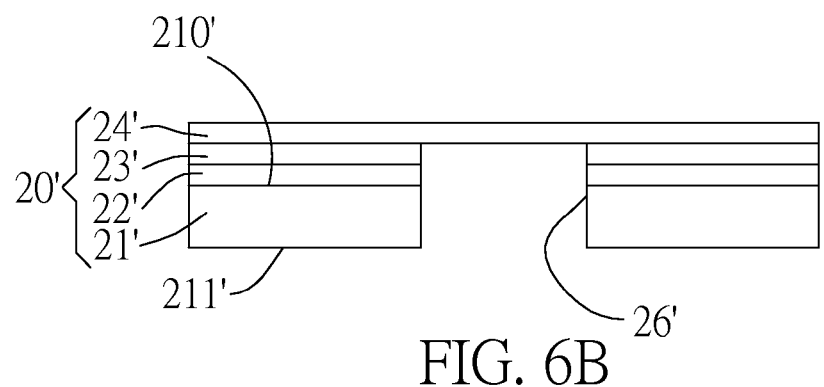

The step shown in FIG. 6B is executed next: removing the first masking layer 1''.

Figure 6C:
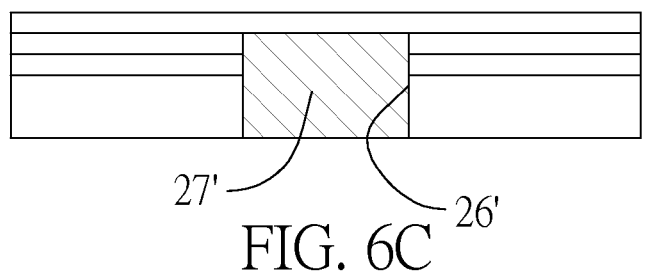

The step shown in FIG. 6C is executed next: filling the drug receiving space 26' with drugs 27'.

Figure 6D:
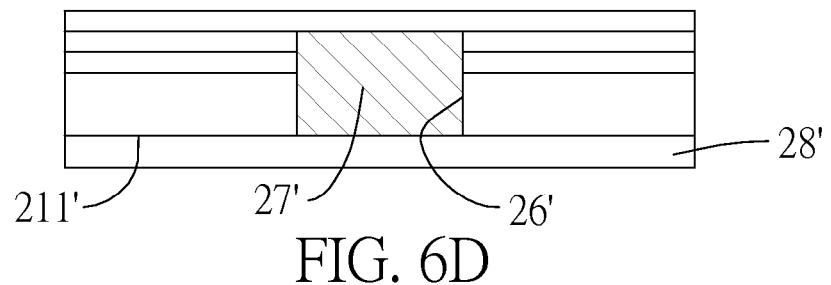

The step shown in FIG. 6D is executed next: installing on the second surface 211' of the substrate 21' a sealing film 28' for sealing up the drugs 27' filled in the drug receiving space 26'.

Figure 7:
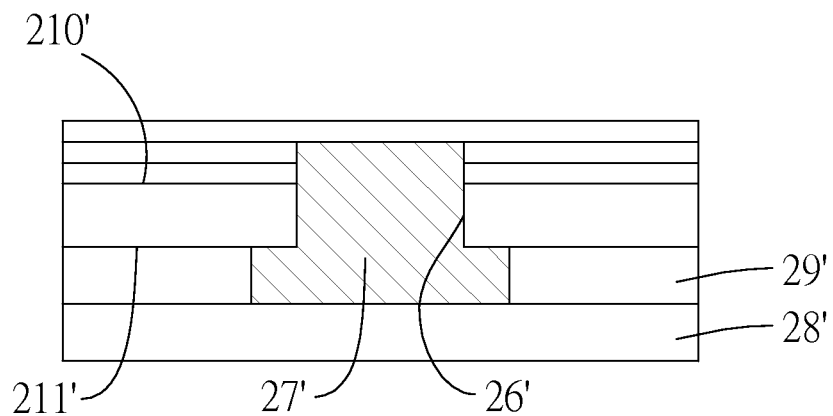
FIG. 7 is a schematic diagram illustrating a step of enlarging a drug receiving space of the drug-delivery chip shown in FIG. 6D.

Please refer to FIG. 7, which is a schematic diagram illustrating a step of enlarging the drug receiving space 26' of the drug-delivery chip. As shown in FIG. 7, a plate layer 29' is installed on the second surface 211' of the substrate 21' at a side edge opposed to a position where the drug receiving space 26' is formed, to enlarge the storage capacity of the drug receiving space 26'. The sealing film 28' is further installed to seal up the drugs 27' filled in the drug receiving space 26'.

Figure 8A:
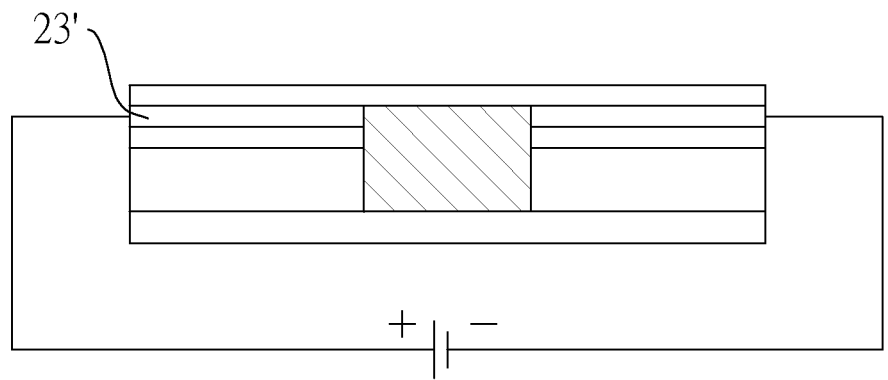
FIGS. 8A and 8B are schematic diagrams illustrating the way that the drug-delivery chip fabricated by the method shown in FIGS. 6A-6D releases drugs.
Figure 8B:
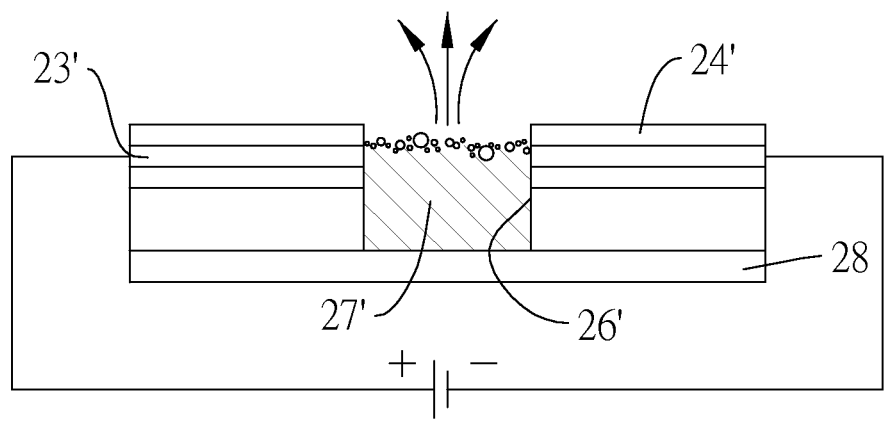

FIGS. 8A-8B illustrate the way that the drug-delivery chip fabricated by the method of fabricating a drug-delivery chip shown in FIGS. 6A-6D releases drugs.

As shown in FIG. 8A, the control module applies voltages to the conductive wire layer 23' according to the actuated signals.

As shown in FIG. 8B, break off the protection layer 24' that covers the drug receiving space 26' to release the drugs 27' received in the drug receiving space 26'.

If the drug-delivery chip has a plurality of drug receiving spaces 26', the drug-delivery chip may further comprise a plurality of switching units connected to the plurality of drug receiving spaces 26' in a one-to-one manner. When the signal-receiving module receives the actuated signals that have check codes, address codes and predetermined time messages, the control module turns on the corresponding switching unit at predetermined time according to the actuated signals, so as to generate a voltage on the conductive wire layer 23', such that the protection layer 24' that covers the drug receiving space 26' is broken off to release the drugs 27'.

The protection layer 24' is broken off because when a current passes through the conductive wire layer 23' the conductive wire layer 23 forms in the drug receiving space 26' an electric field that affects the moisture ($H_2O$) or hydrochloric acid (HCL) contained in the drugs 27' to be electrolyzed and generate hydrogen (H$_2$) and oxygen (O$_2$) bubbles, the swelled bubbles breaking off the protection layer 24' to release the drugs 27'.

In order to speed up the electrolyzed effect, the first masking layer 1" shown in FIG. 6A can cover the conductive wire layer 23' at more positions, allowing the drug receiving space 26' to be formed in a multi-layered conductive wire layer, such that currents pass through the multi-layered conductive wire layer and generate a stronger electric field.

Through a method of fabricating a drug-delivery chip according to the present invention, a drug-delivery technique that has the effectiveness of miniaturization, low cost and the controlling of the drug-delivery time and the kind of drugs to be delivered can be achieved. Compared with the drug-delivery method shown in FIGS. 8A and 8B that employs the electrolyzed way, the drug-delivery method shown in FIGS. 5A and 5B that employs the current heating and melting way needs greater currents, and the amount of the heat generated will be limited to a certain range that does not affect human body or human cells. On the contrary, the drug-delivery method that employs the electrolyzed way does not need great currents. However, in an electrolyzed reaction whether the ingredients and concentration of drugs are changed because of the generation of hydrogen and oxygen due to the electrolyzed reaction has to be considered, while the drugs, through calculation, can have an accurate concentration after the liquid leaves the drugs, without affecting the objectives and effectiveness of the present invention.

Figure 9:
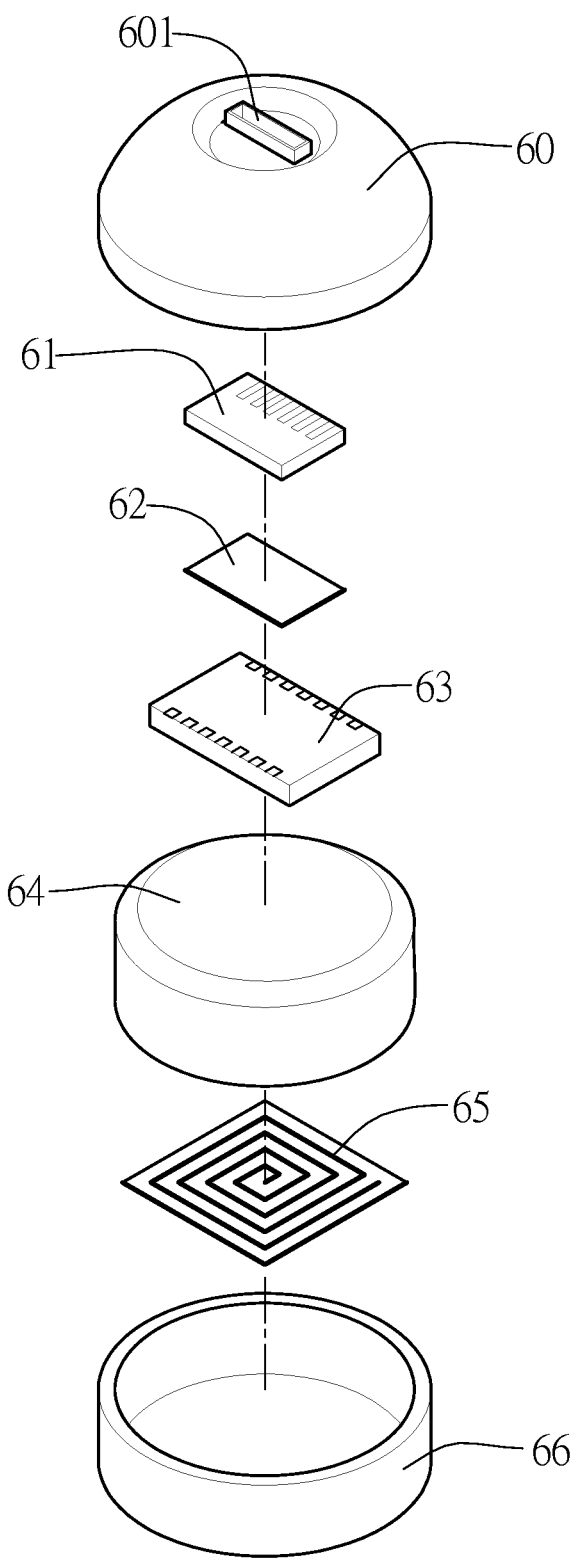
FIG. 9 is a schematic diagram illustrating the packaging of a drug-delivery chip of an embodiment according to the present invention.

FIG. 9 is a schematic diagram illustrating the packaging of a drug-delivery chip of an embodiment according to the present invention, including a top lid 60 having a drug releasing window 601, a drug-delivery chip 61 according to the present invention, a sealing film 62, a circuit board 63, a battery 64, an antenna 65 and a bottom lid 66.

In an embodiment of the present invention, the sealing film 62 is made of an organic material, and covers the drug-delivery chip 61 to seal up the filled drugs; the battery 64 is a chargeable lithium-ion nanowire battery; the circuit board 63 is electrically connected to the drug-delivery chip 61 and the battery 64; and the top lid 60 and the bottom lid 66 are made of a biocompatible material. Therefore, the drug-delivery chip package can be implanted into a living body. Thus, drugs, after being released, will flow to the whole body through the blood circulation, so as to cure the body. Specifically, the drug-delivery chip can be placed in a tumor area, and the drugs of high concentration released by the drug-delivery chip enters the tumor area directly, such that it is unnecessary to increase of the drug concentration in order for the drugs to pass the blood disturbance, which makes the living body feel uncomfortable.

The battery 64 is a lithium-ion nanowire battery, and may be charged wirelessly and stores power. Currents provided by the battery 64 flow through the circuit board 63 to the drug-delivery chip 61. In operation, the circuit board 63 does not consume much power. Therefore, the drug-delivery chip and the method of fabricating the same of the present invention can deliver drugs constantly, without worrying about the power supplying problem.

It can be known from the above embodiments that the application of the drug-delivery chip and the drug-delivery chip package fabricated by a method of fabricating the drug-delivery chip has the effectiveness of miniaturization, low cost, the controlling of drug-delivery time and the kind of drugs to be delivered and constant power and can be implanted into a living body.

Therefore, through the drug-delivery chip and the method of fabricating the same of the present invention, the following objectives can be achieved:

(1) miniaturization and low cost—which is achieved by integrating a signal-receiving module, a drug receiving space and a control module into a single drug-delivery chip, so as to solve the bulky volume and high cost problems of the prior art that employs a circuit board to electrically connect a controller, a signal receiver and a drug storage component;

(2) the controlling of the kind of drugs to be delivered—which is achieved by the control module, which turns on the corresponding switching unit according to the check codes and address codes of the actuated signals, to release the drugs received in the drug receiving space connected to the turned-on switching unit, such that a variety of kinds of drugs can be received in the drug receiving space, depending on various needs; and (3) the controlling of drug-delivery time—which is achieved by transmitting actuated signals at predetermined time, by appending predetermined drug-delivery time messages to the actuated signals and transmitting the actuated signals regularly, or by embedding a predetermined drug-delivery time program into the control module for the release of the drugs received in the drug receiving space.

In sum, the drug-delivery chip and the method of fabricating the same of the present invention integrate a signal-receiving module, a control module and a drug receiving space into a single drug-delivery chip, which combines wireless signals and external currents to enable the drugs received in the drug receiving space to be released, so as to achieve the above objectives and effectiveness.

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. A method of fabricating a drug-delivery chip, comprising the steps of:
    providing a substrate and there being a stack structure comprising an insulation layer, a conductive wire layer having void spaces, and a protection layer on a first surface of the substrate;
    etching the protection layer at a position corresponding to the void spaces of the conductive wire layer to form an opening, wherein the opening is directly above the void spaces;
    forming a metal thin film on the conductive wire layer to seal up the opening, wherein the metal thin film has two ends respectively connected to the conductive wire layer on each of two sides of the opening and is electrically connected to a control module via the conductive wire layer;
    etching the substrate and the insulation layer to form a drug receiving space and expose the metal thin film;
    filling the drug receiving space with a drug; and
    installing a sealing film on a second surface of the substrate to seal up the drug filled in the drug receiving space.

2. The method of claim 1, before the step of the etching the substrate and the insulation layer, further comprising polishing the second surface of the substrate to reduce the thickness of the substrate.

3. The method of claim 1, before the step of the filling the drug receiving space with the drug, further comprising installing a plate layer on the second surface of the substrate at a side edge opposed to a position where the drug receiving space is formed, to enlarge the capacity of the drug receiving space.

4. The method of claim 1, wherein a resistance of the sealing film is greater than a resistance of the conductive wire layer.

5. A method of fabricating a drug-delivery chip, comprising the steps of:
- providing a substrate and there being a stack structure comprising an insulation layer, a conductive wire layer having void spaces, and a protection layer on a first surface of the substrate;
- etching the substrate and the insulation layer at a position corresponding to the void spaces of the conductive wire layer to form a drug receiving space, wherein the drug receiving space is directly over the void spaces;
- filling the drug receiving space with a drug; and
- installing a sealing film on a second surface of the substrate to seal up the drug filled in the drug receiving space.

6. The method of claim 5, before the step of the etching the substrate and the insulation layer, further comprising polishing the second surface of the substrate to reduce the thickness of the substrate.

7. The method of claim 5, before the step of the filling the drug receiving space with the drug, further comprising installing a plate layer on the second surface of the substrate at a side edge opposed to a position where the drug receiving space is formed, to enlarge the capacity of the drug receiving space.

* * * * *